(12) United States Patent
Tanaka et al.

(10) Patent No.: US 6,258,923 B1
(45) Date of Patent: Jul. 10, 2001

(54) METHOD FOR MANUFACTURING DIALKYL CARBONATE

(75) Inventors: Masahide Tanaka; Takato Kimura; Tomoaki Shimoda, all of Ichihara (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/584,672

(22) Filed: May 31, 2000

(30) Foreign Application Priority Data

Jun. 11, 1999 (JP) .................................................. 11-165585

(51) Int. Cl.⁷ ..................................................... C08O 64/00
(52) U.S. Cl. ............................................. 528/196; 528/198
(58) Field of Search ...................................... 528/196, 198

(56) References Cited

U.S. PATENT DOCUMENTS

| 4,218,391 | 8/1980 | Romano et al. ..................... 578/196 |
| 4,785,130 | 11/1988 | Bhattacharya et al. .............. 558/277 |

FOREIGN PATENT DOCUMENTS 2 366 254A    4/1978   (FR) .

Primary Examiner—Terressa M. Boykin

(57) ABSTRACT

An efficient method for manufacturing a dialkyl carbonate from CO, $O_2$, and an alcohol which uses a catalyst comprising:

(i) a cupric halide; and
(ii) a compound capable of producing a copper halide alkoxide by reaction with a cupric halide.

6 Claims, No Drawings

METHOD FOR MANUFACTURING DIALKYL CARBONATE

The present application is a U.S. non-provisional application based upon and claiming priority from Japanese Application No. HEI 11-165585, which is hereby incorporated by reference.

BACKGROUND OF THE INVENTION

The present invention relates to a method for manufacturing a dialkyl carbonate, and more particularly relates to a method for efficiently manufacturing a dialkyl carbonate from CO, $O_2$, and an alcohol.

Because of their excellent impact resistance and other mechanical properties, as well as their excellent heat resistance, transparency, and so on, aromatic polycarbonates have come to be used as engineering plastics in a wide range of fields in recent years.

One method for manufacturing these aromatic polycarbonates that has been put to industrial use is a so-called phosgene process, in which an aromatic dihydroxy compound such as bisphenol is reacted with phosgene by interfacial polycondensation. Unfortunately, numerous problems with this method have been indicated, e.g., extremely toxic phosgene must be used, there is the question of what to do with the large quantity of by-product sodium chloride, and the methylene chloride that is normally used as a reaction solvent can pose health and atmospheric pollution problems.

One known method for manufacturing an aromatic polycarbonate besides the phosgene process is a method (melt method) in which an alkali metal compound such as sodium hydroxide is used as a catalyst in an ester exchange reaction between an aromatic dihydroxy compound and a carbonic diester. This method has garnered attention of late because it has the advantage of allowing an aromatic polycarbonate to be manufactured at lower cost, and it is preferable in terms of environmental safety since it does not involve the use of toxic substances such as phosgene or methylene chloride.

A diaryl carbonate such as diphenyl carbonate is used as the carbonic diester in the manufacture of a polycarbonate by this melt method. As discussed in Japanese Laid-Open Patent Application H9-194430, this diaryl carbonate is manufactured by an ester exchange reaction between a dialkyl carbonate and a hydroxyl group-containing hydrocarbon such as phenol. The dialkyl carbonate that serves as a raw material for this diaryl carbonate is manufactured from carbon monoxide, oxygen, and an alcohol, using a catalyst composed of a cupric halide such as cupric chloride.

For example, when methanol is used as the alcohol, dimethyl carbonate is manufactured by the following reaction.

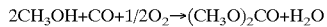

The cupric chloride used as the catalyst here is surmised to form cupric methoxychloride by a primary reaction:

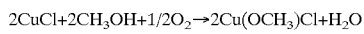

and to be regenerated by a secondary reaction:

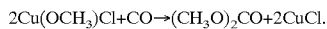

The addition of a hydrohalic acid to the reaction system in order to improve the catalytic activity of the cupric halide used as the catalyst has been disclosed (see Japanese Laid-Open Patent Application H5-194327).

Nevertheless, with a method in which a cupric halide is used as a catalyst as above, the conversion rate at which the above-mentioned cupric alkoxychloride is formed is so low that the yield of the resulting dialkyl carbonate is not necessarily adequate, and furthermore some catalysts can clog the reaction tank and pipes, which is a problem in terms of manufacturing efficiency.

In light of this situation, the inventors conducted diligent investigation into a method for manufacturing a dialkyl carbonate more efficiently, and arrived at the present invention upon discovering that when
 (i) a cupric halide and
 (ii) a compound capable of producing a copper halide alkoxide by reaction with a cupric halide are used together as a catalyst, the reaction proceeds in a state of sustained high catalytic activity, there is no clogging of the reaction tank and pipes by the catalyst, and a carbonic diester is obtained at a high yield.

The present invention was conceived in light of the above prior art, and it is one goal thereof to provide a method for efficiently manufacturing a dialkyl carbonate from CO, $O_2$, and an alcohol.

SUMMARY OF THE INVENTION

The method for manufacturing a dialkyl carbonate pertaining to the present invention is characterized in that a catalyst composed of:
 (i) a cupric halide; and
 (ii) a compound capable of producing a copper halide alkoxide by reaction with a cupric halide
is used in the manufacture of a dialkyl carbonate using carbon monoxide, oxygen, and an alcohol as starting raw materials.

The above-mentioned (ii) compound capable of producing a copper halide alkoxide by reaction with a cupric halide is preferably at least one type of compound selected from the group consisting of alkali metal alkoxides, alkaline earth metal alkoxides, quaternary ammonium alkoxides expressed by the following formula (1), and quaternary phosphonium alkoxides expressed by the following formula (2).

(Where $R^1$ to $R^4$ may be the same as or different from each other, and are each a hydrogen atom or a $C_1$ to $C_{20}$ hydrocarbon group, and $R^5$ is a $C_1$ to $C_{20}$ hydrocarbon group.)

With the present invention, this (ii) compound capable of producing a copper halide alkoxide by reaction with a cupric halide is used in an amount of 0.05 to 2.0 mol with respect to the cupric halide.

Methanol is a preferred alcohol used in the method for manufacturing a dialkyl carbonate pertaining to the present invention.

DETAILED DESCRIPTION OF THE INVENTION

The method for manufacturing a dialkyl carbonate pertaining to the present invention will now be described in specified terms.

First, the starting raw materials and catalysts used in the method for manufacturing a dialkyl carbonate pertaining to the present invention will be described.

Starting Raw Materials and Catalysts

CO, $O_2$, and an alcohol are used as the starting raw materials in the present invention.

There are no particular restrictions on the alcohol used as a starting raw material, but examples include methanol, ethanol, propanol, butanol, isopropanol, isobutanol, and hexanol. Of these, the use of methanol is preferred.

The catalysts in the present invention are (i) a cupric halide and (ii) a compound capable of producing a copper halide alkoxide by reaction with a cupric halide.

Examples of the (i) cupric halide include cupric chloride, cupric fluoride, cupric bromide, and cupric iodide. Of these, the use of cupric chloride is preferred.

One or more types of compound selected from the group consisting of alkali metal alkoxides, alkaline earth metal alkoxides, quaternary ammonium alkoxides expressed by the following formula (1), and quaternary phosphonium alkoxides expressed by the following formula (2) can be used favorably as the (ii) compound capable of producing a copper halide alkoxide by reaction with a cupric halide.

$$R^1R^2R^3R^4NOR^5 \tag{1}$$

$$R^1R^2R^3R^4POR^5 \tag{2}$$

(Where $R^1$ to $R^4$ may be the same as or different from each other, and are each a hydrogen atom or a $C_1$ to $C_{20}$ hydrocarbon group, and $R^5$ is a $C_1$ to $C_{20}$ hydrocarbon group.)

Specific examples of alkali metal alkoxides include sodium methoxide, lithium methoxide, potassium methoxide, rubidium methoxide, cesium methoxide, sodium ethoxide, lithium ethoxide, potassium ethoxide, rubidium ethoxide, cesium ethoxide, sodium propoxide, lithium propoxide, potassium propoxide, rubidium propoxide, cesium propoxide, sodium butoxide, lithium butoxide, potassium butoxide, rubidium butoxide, cesium butoxide, sodium pentoxide, lithium pentoxide, potassium pentoxide, rubidium pentoxide, cesium pentoxide, sodium hectoxide, lithium hectoxide, potassium hectoxide, rubidium hectoxide, cesium hectoxide, sodium heptoxide, lithium heptoxide, potassium heptoxide, rubidium heptoxide, cesium heptoxide, sodium octoxide, lithium octoxide, potassium octoxide, rubidium octoxide, cesium octoxide, sodium phenoxide, lithium phenoxide, potassium phenoxide, rubidium phenoxide, and cesium phenoxide.

Specific examples of alkaline earth metal alkoxides include mono- and dialkoxide compounds such as methoxides, ethoxides, propoxides, butoxides, pentoxides, hectoxides, heptoxides, octoxides, and phenoxides of beryllium, magnesium, calcium, strontium, and barium.

Specific examples of quaternary ammonium alkoxides include alkoxide compounds such as methoxides, ethoxides, propoxides, butoxides, pentoxides, hectoxides, heptoxides, octoxides, and phenoxides of tetramethylammonium, tetraethylammonium, tetrapropylammonium, tetrabutylammonium, tetrapentylammonium, tetraheptylammonium, tetraoctylammonium, and tetraphenylammonium.

Specific examples of quaternary phosphonium alkoxides include alkoxide compounds such as methoxides, ethoxides, propoxides, butoxides, pentoxides, hectoxides, heptoxides, octoxides, and phenoxides of tetramethylphosphonium, tetraethylphosphonium, tetrapropylphosphonium, tetrabutylphosphonium, tetrapentylphosphonium, tetraheptylphosphonium, tetraoctylphosphonium, and tetraphenylphosphonium.

The above-mentioned (i) cupric halide and (ii) a compound capable of producing a copper halide alkoxide by reaction with a cupric halide are thought to produce a copper halide alkoxide by reacting as shown in the following formula (3).

$$(i)CuX_2 + (ii)M(OR')_n \rightarrow Cu(OR')X + MX(OR')_{n-1} \tag{3}$$

(In the formula, X is a halogen, M is an alkali metal, alkaline earth metal, quaternary ammonium, or quaternary phosphonium, n is the valence of M, and R is a $C_1$ to $C_{20}$ hydrocarbon group.)

This copper halide alkoxide exhibits high catalytic activity in the manufacture of a dialkyl carbonate using carbon monoxide, oxygen, and an alcohol as the starting raw materials, and furthermore is stable during the reaction, so the activity of the catalyst can be maintained over an extended period.

A copper halide alkoxide can even be formed with the cuprous chloride used in the past, by the following reaction during the reaction discussed above.

$$2CuCl + 2CH_3OH + 1/2O_2 \rightarrow 2Cu(OCH_3)Cl + H_2O$$

The efficiency of producing a copper halide alkoxide is low with this reaction, however, and as a result, the dialkyl carbonate productivity is often low. Also, if the above-mentioned alkoxy compound (the compound capable of producing a copper halide alkoxide by reaction with a cupric halide) is added to this cuprous chloride, the following reaction will proceed, making it difficult for a copper halide alkoxide to form.

$$2CuX + (ii)M(OR')_n \rightarrow Cu(OR') + MX(OR')_{n-1}$$

In contrast, using (i) a cupric halide and (ii) a compound capable of producing a copper halide alkoxide by reaction with a cupric halide as in the present invention allows a copper halide alkoxide to be produced very efficiently. Accordingly, the present invention makes it possible to manufacture a dialkyl carbonate stably over an extended period.

With the present invention, it is preferable for this (ii) compound capable of producing a copper halide alkoxide by reaction with a cupric halide to be used in an amount of 0.05 to 2.0 mol, and even more preferably 0.1 to 1.2 mol, with respect to the cupric halide.

Manufacture of the dialkyl carbonate

With the present invention, the above-mentioned catalysts are used in the manufacture of a dialkyl carbonate using carbon monoxide, oxygen, and an alcohol as starting raw materials.

More specifically, first, (i) a cupric halide and (ii) a compound capable of producing a copper halide alkoxide by reaction with a cupric halide are added to and reacted with the alcohol that is one of the raw materials to prepare a raw material alcohol containing catalyst components. It is preferable for the cupric halide to be used in an amount of 0.001 to 1.0 mol, and even more preferably 0.005 to 0.2 mol, per mole of alcohol. If needed here, a hydrohalic acid may be added along with the (i) cupric halide and the (ii) compound capable of producing a copper halide alkoxide by reaction with a cupric halide.

Next, a gas of carbon monoxide and oxygen is introduced under pressure into the alcohol containing catalyst components. The carbon monoxide and the oxygen may be supplied individually to the alcohol containing catalyst components, or they may be mixed first and then supplied. Here, a gas that will not generate a reaction product may be present in the reaction system, specific examples of which include hydrogen, nitrogen, carbon dioxide, methane, argon, and other such inert gases.

The amount of carbon monoxide that is introduced should be greater than the stoichiometric amount. Therefore, the molar ratio in which the carbon monoxide and oxygen are introduced (carbon monoxide/oxygen) should be from 3/1 to 100/1, and preferably from 20/1 to 100/1.

The reaction is usually conducted at a temperature of 50 to 200° C., and preferably 100 to 150° C., and at a pressure between atmospheric pressure and 150 atm, and preferably between 10 and 100 atm.

The present invention allows the yield of the resulting dialkyl carbonate to be increased.

The dialkyl carbonate that is produced can be recovered by employing a standard separation method, such as distillation, filtration, decantation, centrifugation, demixing, or osmotic membrane separation. A combination of two or more of these methods may also be used.

The cupric halide, the compound capable of producing a copper halide alkoxide by reaction with a cupric halide, any unreacted alcohol, and the like contained in the reaction solution after the recovery of the produced dialkyl carbonate can also be recovered and reused.

This reaction can be carried out using a batch type of reactor or a continuous reactor. An autoclave or other such pressure-resistant vessel can also be used.

When a continuous reactor is used, the alcohol, carbon monoxide, and oxygen are reacted by supplying an alcohol containing a cupric halide and a compound capable of producing a copper halide alkoxide by reaction with a cupric halide into a solution. Next, the reaction solution containing the produced dialkyl carbonate, water, and alcohol, and the unreacted carbon monoxide and water vapor are taken out, the dialkyl carbonate and water are removed from the reaction solution, and the other components are recirculated back to the reaction system.

Any dialkyl carbonate that has not been recovered may be contained in the reaction solution to which an alcohol, carbon monoxide, oxygen, and, if necessary, a hydrohalic acid are supplied. The reaction solution to which an alcohol, carbon monoxide, oxygen, and, if necessary, a hydrohalic acid are supplied should have an alcohol concentration of 30 to 80 wt %, and preferably 35 to 80 wt %, and a water concentration of 1 to 10 wt %, and preferably 2 to 7 wt %.

With this method for manufacturing a dialkyl carbonate pertaining to the present invention, (ii) a compound capable of producing a copper halide alkoxide by reaction with a cupric halide is used along with (i) a cupric halide. Consequently, it is possible with the present invention to manufacture a dialkyl carbonate efficiently at a sustained level of high catalytic activity.

The method for manufacturing a dialkyl carbonate pertaining to the present invention allows a dialkyl carbonate to be manufactured efficiently in a state of sustained high catalytic activity, with no clogging of the reaction tank and pipes by the catalyst. Also, if the polycondensation of a polycarbonate is performed using a diaryl carbonate manufactured using a dialkyl carbonate obtained in this manner as a raw material, it will be possible to obtain a polycarbonate with improved coloring, and this polycarbonate will be suitable not only for general molding materials, but also for sheeting and other such construction materials, automotive headlamp lenses, eyeglasses and other such optical lenses, optical recording materials, and so forth, and will be particularly favorable as a material for molding optical disks.

WORKING EXAMPLES

The present invention will now be described in more specific terms through working examples, but the present invention is not limited to or by these examples.

The properties discussed in the working examples of the present invention were measured as follows.

Working Example 1

47.2 g of methanol, 6.90 g of cupric chloride, and 1.38 g of sodium methoxide (NaOMe/$CuCl_2$ molar ratio=0.5) were supplied to an autoclave made of Hastelloy and having an internal volume of 300 mL, and the autoclave was sealed.

Next, the temperature in the autoclave was raised to 125° C., reaction gas (composition: 5.55% $O_2$, 5.78% $N_2$, 88.7% CO, and 0.01% $CO_2$) was supplied to the autoclave at a rate of 31.0 mL/g such that the overall pressure was 25 to 26 kg/cm$^2$·G, and a reaction was conducted for 60 minutes.

After the autoclave had cooled, the unreacted gas was slowly purged, the reaction solution was taken out, and the reacted gas composition and the reaction solution composition were quantified and analyzed by gas chromatography.

These results are given in Table 1.

The dimethyl carbonate conversion rate from methanol was 8.6 mol %, and the amount of dimethyl carbonate produced was 5.7 g.

Methylal was confirmed as a by-product.

Working Example 2

47.0 g of methanol, 6.91 g of cupric chloride, and 1.96 g of sodium methoxide (NaOMe/$CUCl_2$ molar ratio=0.71) were supplied to an autoclave made of Hastelloy and having an internal volume of 300 mL, and the autoclave was sealed.

Next, the temperature in the autoclave was raised to 125° C., the same reaction gas as that used in Working Example 1 was supplied to the autoclave at a rate of 36.5 mL/g such that the overall pressure was 21.5 to 24 kg/cm$^2$·G and a reaction was conducted for 60 minutes.

After the autoclave had cooled, the unreacted gas was slowly purged, the reaction solution was taken out, and the reacted gas composition and the reaction solution composition were quantified and analyzed by gas chromatography.

These results are given in Table 1.

The dimethyl carbonate conversion rate from methanol was 9.7 mol %, and the amount of dimethyl carbonate produced was 6.4 g.

Methylal was confirmed as a by-product.

Working Example 3

46.2 g of methanol, 6.90 g of cupric chloride, and 1.85 g of potassium methoxide (KOMe/$CuCl_2$ molar ratio=0.5) were supplied to an autoclave made of Hastelloy and having an internal volume of 300 mL, and the autoclave was sealed.

Next, the temperature in the autoclave was raised to 125° C., reaction gas (composition: 5.55% $O_2$, 5.78% $N_2$, 88.7% CO, and 0.01% $CO_2$) was supplied to the autoclave at a rate of 31.0 mL/g such that the overall pressure was 25 to 26 kg/cm$^2$·G, and a reaction was conducted for 60 minutes.

After the autoclave had cooled, the unreacted gas was slowly purged, the reaction solution was taken out, and the reacted gas composition and the reaction solution composition were quantified and analyzed by gas chromatography.

These results are given in Table 1.

The dimethyl carbonate conversion rate from methanol was 9.2 mol %, and the amount of dimethyl carbonate produced was 6.0 g.

Methylal was confirmed as a by-product.

Working Example 4

47.0 g of methanol, 6.91 g of cupric chloride, and 1.96 g of sodium methoxide (NaOMe/$CuCl_2$ molar ratio=0.71)

were supplied to an autoclave made of Hastelloy and having an internal volume of 300 mL, and the autoclave was sealed.

Next, the temperature in the autoclave was raised to 125° C., the same reaction gas as that used in Working Example 1 was supplied to the autoclave at a rate of 36.5 mL/g such that the overall pressure was 24.5 to 25.0 kg/cm².G, and a reaction was conducted for 150 minutes.

After the autoclave had cooled, the unreacted gas was slowly purged, the reaction solution was taken out, and the reacted gas composition and the reaction solution composition were quantified and analyzed by gas chromatography. These results are given in Table 1.

The dimethyl carbonate conversion rate from methanol was 13.9 mol %, and the amount of dimethyl carbonate produced was 6.90 g.

Methylal was confirmed as a by-product.

Comparative Example 1

47.1 g of methanol and 6.90 g of cupric chloride were supplied to an autoclave made of Hastelloy and having an internal volume of 300 mL, and the autoclave was sealed. Next, the temperature in the autoclave was raised to 125° C., reaction gas (composition: 5.07% $O_2$, 6.15% $N_2$, 88.8% CO, and 0.01% $CO_2$) was supplied to the autoclave at a rate of 31.0 mL/g such that the overall pressure was 24 to 25 kg/cm².G, and a reaction was conducted for 60 minutes.

After the autoclave had cooled, the unreacted gas was slowly purged, the reaction solution was taken out, and the reacted gas composition and the reaction solution composition were quantified and analyzed by gas chromatography. These results are given in Table 1.

The dimethyl carbonate conversion rate from methanol was 4.7 mol %, and the amount of dimethyl carbonate produced was 3.1 g.

Comparative Example 2

47.2 g of methanol and 5.08 g of cuprous chloride were supplied to an autoclave made of Hastelloy and having an internal volume of 300 mL, and the autoclave was sealed.

Next, the temperature in the autoclave was raised to 125° C., reaction gas (composition: 5.44% $O_2$, 3.62% $N_2$, 90.9% CO, and 0.01% $CO_2$) was supplied to the autoclave at a rate of 26.6 mL/g such that the overall pressure was 25 to 26 kg/cm².G, and a reaction was conducted for 60 minutes.

After the autoclave had cooled, the unreacted gas was slowly purged, the reaction solution was taken out, and the reacted gas composition and the reaction solution composition were quantified and analyzed by gas chromatography. These results are given in Table 1.

The dimethyl carbonate conversion rate from methanol was 5.4 mol %, and the amount of dimethyl carbonate produced was 3.6 g.

Comparative Example 3

47.2 g of methanol and 5.08 g of cuprous chloride were supplied to an autoclave made of Hastelloy and having an internal volume of 300 mL, and the autoclave was sealed.

Next, the temperature in the autoclave was raised to 125° C., reaction gas (composition: 5.44% $O_2$, 3.62% $N_2$, 90.9% CO, and 0.01% $CO_2$) was supplied to the autoclave at a rate of 26.6 mL/g such that the overall pressure was 25 to 26 kg/cm².G, and a reaction was conducted for 150 minutes.

After the autoclave had cooled, the unreacted gas was slowly purged, the reaction solution was taken out, and the reacted gas composition and the reaction solution composition were quantified and analyzed by gas chromatography. These results are given in Table 1.

The dimethyl carbonate conversion rate from methanol was 9.5 mol %, and the amount of dimethyl carbonate produced was 6.3 g.

TABLE 1

|  | Catalyst components | | | | Reaction time (min.) | Amount of dimethyl carbonate produced (g) |
| --- | --- | --- | --- | --- | --- | --- |
|  | Methanol (g) | $CuCl_2$ (g) | CuCl (g) | Alkoxide compound (g) | | |
| Working Example 1 | 47.2 | 6.90 | — | NaOMe:1.38 | 60 | 5.70 |
| Working Example 2 | 47.0 | 6.91 | — | NaOMe:1.96 | 60 | 6.41 |
| Working Example 3 | 46.2 | 6.90 | — | KOMe:1.85 | 60 | 6.00 |
| Working Example 4 | 47.0 | 6.91 | — | NaOMe:1.96 | 150 | 9.20 |
| Comparative Example 1 | 47.1 | 6.92 | — | — | 60 | 3.14 |
| Comparative Example 2 | 47.2 | — | 5.08 | — | 60 | 3.60 |
| Comparative Example 3 | 47.2 | — | 5.08 | — | 150 | 6.30 |

What is claimed is:

1. A method for manufacturing a dialkyl carbonate using carbon monoxide, oxygen, and an alcohol as starting raw materials, said method for manufacturing a dialkyl carbonate comprising use of a catalyst consisting essentially of:
(i) a cupric halide; and
(ii) a compound capable of producing a copper halide alkoxide by reaction with the cupric halide.

2. A method for manufacturing a dialkyl carbonate as defined in claim 1, wherein the (ii) compound capable of producing a copper halide alkoxide by reaction with a cupric halide comprises at least one type of compound selected from the group consisting of alkali metal alkoxides, alkaline earth metal alkoxides, quaternary ammonium alkoxides expressed by the following formula (1), and quaternary phosphonium alkoxides expressed by the following formula (2)

$R^1R^2R^3R^4NOR^5$ (1)

$R^1R^2R^3R^4POR^5$ (2), wherein $R^1$ to $R^4$ may be the same as or different from each other, and are each a hydrogen atom or a $C_1$ to $C_{20}$ hydrocarbon group, and $R^5$ is a $C_1$ to $C_{20}$ hydrocarbon group.

3. A method for manufacturing a dialkyl carbonate according to claim 1, wherein the (ii) compound capable of producing a copper halide alkoxide by reaction with a cupric halide is used in an amount of 0.05 to 2.0 mole with respect to the moles of cupric halide.

4. A method for manufacturing a dialkyl carbonate according to claim 1, wherein, the alcohol is methanol.

5. A method of making polycarbonate which comprises transesterifying an aromatic dihydroxy method together with a diaryl carbonate, wherein the diaryl carbonate is made by an ester exchange reaction between a dialkyl carbonate and a hydroxyl group-containing hydrocarbon, wherein the dialkyl carbonate is made by the process according to claim 1.

6. A method for manufacturing a dialkyl carbonate using carbon monoxide, oxygen, and an alcohol as starting raw materials, said method for manufacturing a dialkyl carbonate comprising use of a catalyst consisting essentially of:
(i) a cupric halide;
(ii) a compound capable of producing a copper halide alkoxide by reaction with the cupric halide; and
(iii) a hydrohalic acid.

* * * * *